United States Patent [19]

Gauglitz

[11] Patent Number: 5,231,990
[45] Date of Patent: Aug. 3, 1993

[54] APPLICATION SPECIFIC INTEGRATED CIRCUIT FOR PHYSIOLOGICAL MONITORING

[75] Inventor: Karl F. Gauglitz, Redmond, Wash.

[73] Assignee: SpaceLabs, Medical, Inc., Redmond, Wash.

[21] Appl. No.: 911,015

[22] Filed: Jul. 9, 1992

[51] Int. Cl.$^5$ ............................................. A61N 1/00
[52] U.S. Cl. ................... 128/697; 128/699; 128/696; 364/413.06; 607/27
[58] Field of Search ......... 128/696, 697, 699, 419 PT, 128/708; 364/413.02, 413.03, 413.05, 413.06

[56] References Cited

U.S. PATENT DOCUMENTS

| | | | |
|---|---|---|---|
| 3,991,747 | 11/1976 | Stanly et al. | 128/419 PT |
| 4,117,848 | 10/1978 | Naylor | 128/419 PT |
| 4,121,576 | 10/1978 | Greensite | 128/699 |
| 4,159,018 | 6/1979 | Brastad | 128/697 |
| 4,697,597 | 10/1987 | Sanz et al. | 128/699 |
| 4,850,367 | 7/1989 | Rantala | 128/670 |
| 4,934,376 | 6/1990 | Armington | 128/697 |
| 5,002,063 | 3/1991 | Haner | 128/696 |

FOREIGN PATENT DOCUMENTS

| | | | |
|---|---|---|---|
| WO83/04369 | 12/1983 | PCT Int'l Appl. | 128/696 |
| 2207579A | 2/1989 | United Kingdom | 128/696 |

OTHER PUBLICATIONS

Grossbach, Wolfgang, "Measuring the ECG Signal with a Mixed Analog-Digital Application-Specific IC," Hewlett-Packard Journal, pp. 21-24, Oct. 1991.

*Primary Examiner*—William E. Kamm
*Assistant Examiner*—George Manuel
*Attorney, Agent, or Firm*—Seed and Berry

[57] ABSTRACT

An application specific integrated circuit (ASIC) for physiological monitoring that has multiple inputs and outputs for flexible system architecture in which multiple ASICs are easily coupled together to expand the number of channels being monitored. Each ASIC has multiple inputs that may be coupled to the patient and analog expansion inputs to accept signals from other ASICs. A buffered version of the patient inputs allows signals to be transferred to other ASICs. A lead summing network, under control of lead select and system configuration lines, sums the patient inputs, the expansion inputs, or both, to produce various signal leads. Multiple ASICs are easily coupled together to produce any number of signal lead combinations. In one embodiment, the ASIC is used for ECG monitoring and has inputs coupled to patient electrodes and buffered versions of each patient input. The ASIC also has expansion inputs to accept signals from other ASICs. A single ASIC can operate in a standard mode for three-lead or five-lead operation or in the Holter monitor mode. The ASIC also has pacer detection circuitry to detect standard pacer pulses and bioimpedance pulses even in the presence of respiration monitoring signals. The system can be expanded using two ASICs for twelve-lead ECG monitoring or three ASICs for fifteen-lead monitoring. The ASIC also includes circuitry for lead drive and lead fault detection, pacer delay, blanking, trace recovery circuit, programmable bandpass filters, programmable gain amplifiers, an analog multiplexor and sample/hold circuit to allow easy interface to an external analog to digital convertor.

58 Claims, 7 Drawing Sheets

APPLICATION SPECTIFIC INTEGRATED CIRCUIT FOR PHYSIOLOGICAL MONITORING

DESCRIPTION

1. Technical Field

The present invention relates to an apparatus for processing multiple analog signals. More specifically, the present invention relates to an application-specific integrated circuit (ASIC) for physiological monitoring.

2. Background of the Invention

Modern medical instrumentation has greatly increased the ability of health care workers to monitor and diagnose the physiological condition of a patient. In addition to meeting numerous safety standards, modern medical instrumentation must operate satisfactorily in an environment where other medical instruments and sources of interference can potentially lead to a decrease in the quality of performance. Furthermore, medical instrumentation must be flexible enough in design to meet new and unexpected user requirements.

To meet the demand of satisfactory operation in a harsh environment, medical instrumentation is often designed in a manner which limits the flexibility of operation. For example, electrocardiography (ECG) monitoring in a surgical environment where electrosurgical radio frequency interference (RFI) is present requires careful filtering of the ECG signals as well as an attempt to minimize capacitance between the ECG circuit isolated analog ground and the AC power line or the chassis ground. If features such as respiration monitoring or heart pacer detection capability are added to a monitor system, the ECG circuitry must be able to operate in the presence of these interfering signals as well. As a result, the ECG monitor circuitry has grown in complexity and cannot easily be expanded to accommodate a different number of electrode inputs.

The increased complexity of ECG monitor circuitry requires that the ECG monitor circuitry occupy a great deal of space on a printed circuit board. Additional features such as lead drive circuitry to reduce common-mode signals, and lead fault circuitry occupy more space on a printed circuit board. To overcome this problem, some manufacturers use an application-specific integrated circuit (ASIC) which incorporates much of the complex circuitry into a single integrated circuit. For example, some prior art systems incorporate a complete three-channel ECG monitor into a single data acquisition ASIC. The drawback to this approach is that the ASIC cannot be easily expanded to incorporate monitoring of five-lead or fifteen-lead ECG monitoring. Furthermore, the prior art system cannot be configured for a Holter monitor ECG, which uses three pairs of bipolar inputs.

Therefore, it can be appreciated that there is a significant need for an ASIC which incorporates advanced features such as pacer and bioimpedance pulse detection and allows for easy expansion to monitor any number of ECG signal leads.

SUMMARY OF THE INVENTION

The present invention resides in an application specific integrated circuit (ASIC) for use with physiological monitoring. The ASIC has flexible system architecture allowing the use of one or more ASICs within a monitoring system. In one embodiment, a single ASIC may be used for three-lead or five-lead ECG monitoring. The ASIC may be easily configured for Holter monitor configuration in which the electrodes are bipolar, or in the standard lead configuration which uses unipolar electrodes. If additional leads are desired, such as twelve-lead or fifteen-lead ECG monitoring, additional ASICs may be easily added. Each ASIC contains a plurality of analog inputs which may be coupled to the patient in various configurations. A buffered version of the analog inputs is made available for expansion with multiple ASICs. A plurality of digital control lines control the manner in which the analog inputs are connected within a lead summing network. The outputs from the lead summing network provide various vectors used in physiological monitoring. In one embodiment, the vectors are processed further by analog filters and amplifiers. An analog multiplexor selects a vector to couple to a sample/hold circuit within the inventive ASIC. A sample/hold circuit allows easy interface with an external analog to digital convertor.

In one embodiment of the invention, the ASIC is tailored for ECG monitoring and includes seven analog inputs which may be coupled to the patient in various configurations. The digital control lines control the manner in which the analog inputs are connected within the lead summing network. The lead summing network has six summed outputs which provides various standard ECG lead configurations. The summed leads are monitored by a pacer detect circuit which can detect heart pacemaker pacer pulses. The ECG signals are blanked for various periods of time depending on the type of pacer pulse detected by the pacer detect circuit. The summed leads are filtered and amplified in the manner described above. The analog multiplexor selects one of the summed lead inputs or the positive or negative peak pulse signals from the pacer detect circuit and couples the selected signal to the sample/hold circuit.

In one embodiment, the invention also includes a pacer detect circuit capable of determining the pulse width of typical heart pacemaker pulses and shorter bioimpedance pulses used in some demand pacemakers. In addition to determining the pulse width, the inventive pacer detect circuit can determine the polarity of the pacer pulse and the amplitude. In one embodiment of the pacer detect circuit, the peak positive and negative amplitudes are made available so that the pacer pulse itself can be analyzed.

Other features and advantages of the circuit will become apparent from the following detailed description, taken in conjunction with the accompanying drawings.

DETAILED DESCRIPTION OF THE INVENTION

Figure 1:
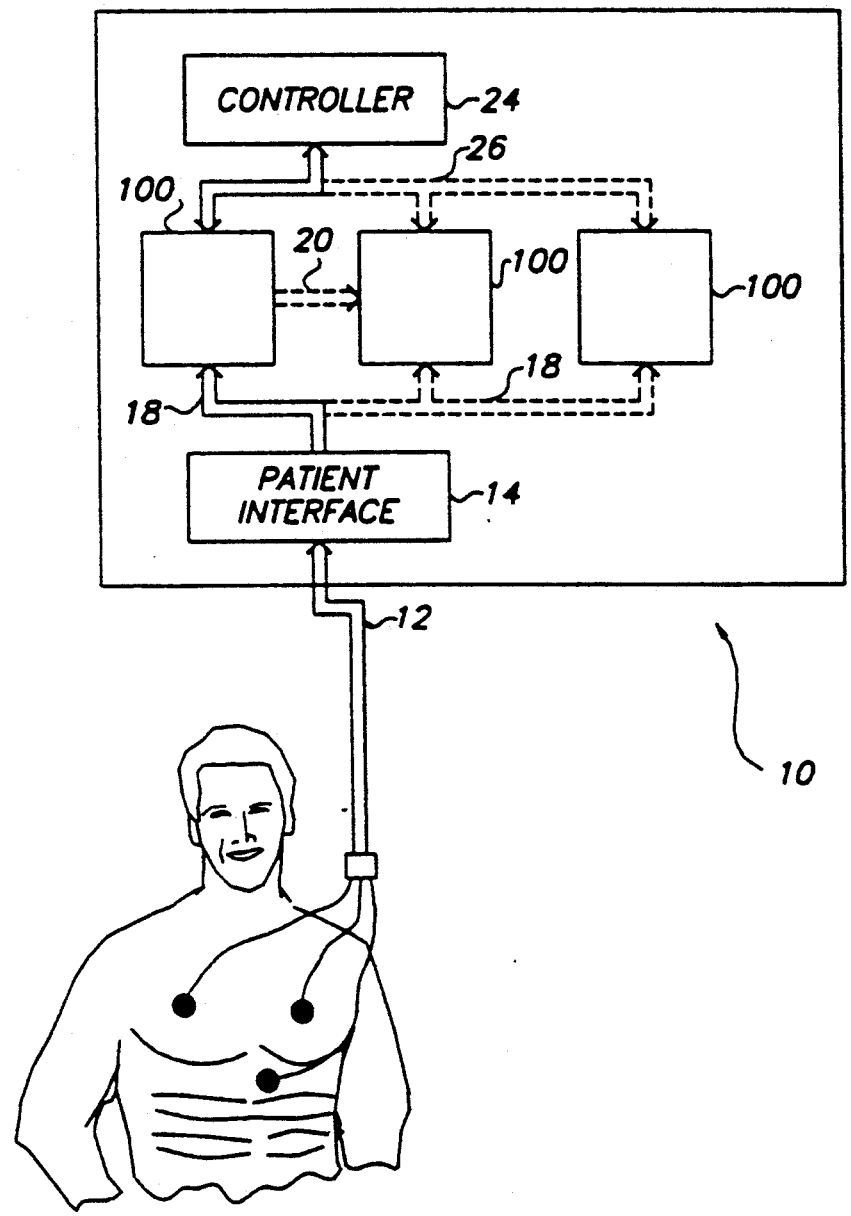
FIG. 1 is a system block diagram portraying a physiological monitoring system incorporating one or more of the inventive integrated circuits.

The present invention resides in an application specific integrated circuit (ASIC) used for physiological monitoring. One or more of the inventive ASICs 100 are incorporated into a physiological monitor system 10 as shown in the system block diagram of FIG. 1. The patient is coupled to the monitor system 10 through a patient cable 12. The patient cable 12 couples the low level physiological signals to a patient interface circuit 14 within the monitor system 10. The patient interface circuit 14 couples the physiological signals to one or more ASICs 100 through a signal bus 18. If multiple ASICs are used within the monitor system 10, selected patient signals may be coupled from one ASIC to another via an expansion signal bus 20. A more detailed description of interconnection of multiple ASICs 100 is provided below. The ASICs 100 are controlled by a controller 24 which may be a computer or a digital controller such as a programmable array logic (PAL) device. The controller 24 is coupled to the one or more ASICs 100 via a control bus 26.

The ASIC is used for ECG monitoring and incorporates numerous features not available in a single integrated circuit, including pacer and bioimpedance pulse detection circuitry and analog input and output circuitry to allow easy expansion with multiple ASICs.

The ECG electrode leads 12 connected to the patient couple the low level analog physiological signals to the ECG monitor system 10. Patient interface circuitry 14 such as an input spark gap protection circuit, resistor networks and termination resistor networks are external to the inventive ASIC 100. The function of the patient interface circuitry 14 is well known to those skilled in the art and will not be discussed herein.

Figure 2:
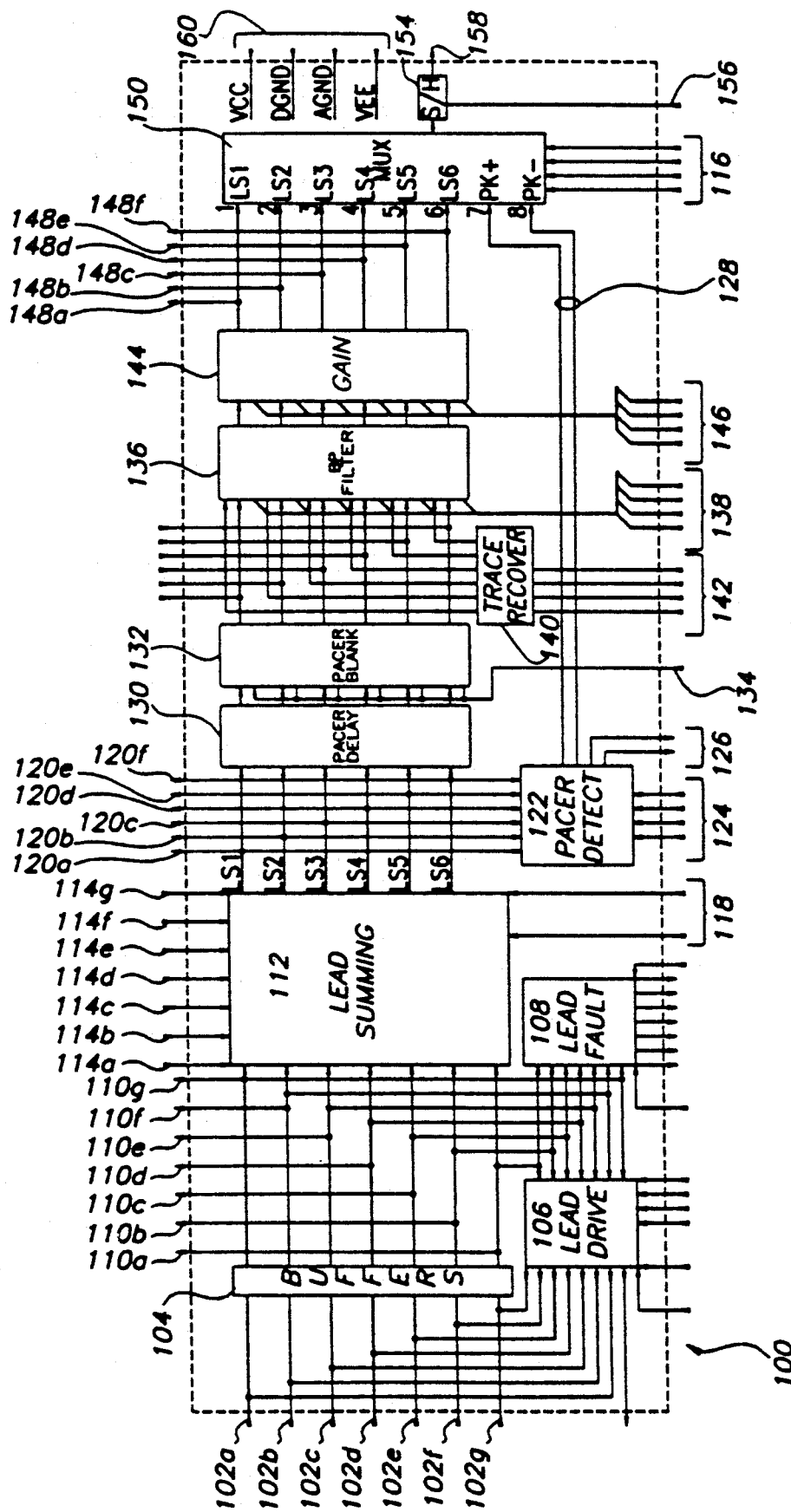
FIG. 2 is a functional block diagram of the integrated circuit of the present invention.

The presently preferred embodiment of the inventive ASIC 100 comprises seven analog input channels 102a-g which are coupled to a buffer 104 as shown in FIG. 2. A lead drive circuit 106 and a lead fault circuit 108 are also incorporated into the ASIC 100. The buffered analog signals are coupled to both analog signal output terminals 110a-g and a lead summing network 112. The analog signal output terminals 110a-g are used with multiple ASICs as will be described in detail below. In addition to the buffered signals as inputs to the lead summing network 112, there are also a plurality of analog expansion inputs 114a-g as inputs to the lead summing network 112. The analog expansion inputs 114a-g are used with multiple ASICs as will be described in detail below.

The lead summing network 112 responds to a set of lead selection signals 116 and system configuration signals 118 to select various combinations of inputs to sum together. The lead selection outputs 120a-f from the lead summing network 112 are coupled to a pacer detect circuit 122, which can detect both typical heart pacemaker signals and shorter-duration bioimpedance pulses. Pacer detect lead select control lines 124 are used to select which lead from the lead summing network 112 will be analyzed by the pacer detect circuit 122. The pacer detect circuit 122 generates pacer pulse status outputs 126 that indicate the rising and falling edge of pacer signals. The pacer detect circuit 122 also detects both the positive and negative peak amplitudes of pacer signals and provides the peak amplitude signals as additional outputs 128 from the pacer detect circuit 122.

The lead selection outputs 120a-f of the lead summing network 112 are also coupled to a pacer delay network 130. The outputs of the pacer delay network 130 are coupled to a pacer blanking network 132. The pacer blanking network 132, in response to a pacer blanking control line 134, selectively blanks the signals from the pacer delay network 130. The analog signals from the pacer blanking network 132 are filtered by a programmable bandpass filter network 136. The bandpass filter control lines 138 are used to select predetermined filter bandwidths. A trace recovery circuit 140 is used to restore an analog signal baseline in the event of a signal overload. Trace recovery control lines 142 determine which analog signal baseline will be restored.

The analog signals from the bandpass filters 136 are amplified by a programmable gain amplifier network 144. The programmable gain control lines 146 select predetermined gains for each analog signal. The analog output signals from the programmable gain amplifier network 144 are coupled to amplified analog output terminals 148a-f and to the inputs of an analog In addition to the analog output signals from the programmable gain amplifier 144, the peak amplitude signals 128 from the pacer detector 122 are also inputs to the analog multiplexor 150. The lead selection signals 116, which control the operation of the lead summing network 112, also control the channel selection of the analog multiplexor 150.

The output of the analog multiplexor 150 is coupled to the input of a sample and hold circuit 154. A sample and hold control line 156 determines the mode of operation of the sample and hold circuit 154. The output of the sample and hold circuit 154 is coupled to the ASIC output terminal 158. Power is supplied to the ASIC 100 through the power supply terminals 160.

The ASIC output terminal 158 can be externally coupled to an analog to digital converter (ADC) (not shown). An external ADC is utilized for maximum design flexibility. In applications calling for low resolution, a less expensive ADC may be used. In other applications, such as diagnostic ECG monitoring, a more expensive high-resolution ADC may be used. In some applications, an ADC may not be used at all. The analog output terminals 148a-f may be used to couple analog signals directly to external analog devices such as a Holter recorder.

As a more detailed description of the inventive ASIC 100, the buffer 104 is coupled to the analog signal inputs 102a-g as shown in FIG. 2. The analog signal inputs 102 a-g couple the analog physiological signals from the patient to the ASIC 100. As previously noted, there may be external patient interface circuitry 14 (see FIG. 1) within the system monitor to provide patient interface with the ASIC 100. The operation lead drive circuit 106 is well known to those skilled in the art. The common mode signal from selected patient input leads is derived from the buffer 104, and an inverted version of the common mode signal is actively supplied to the driven lead on the patient. This inverted common mode signal helps reduce the common mode signal present on the patient and increases the overall common mode rejection in the monitor system. The lead drive circuit 106 derives the common mode signal and the inverted signal and drives the selected lead with the inverted signal. The standard industry practice is to drive the right leg (RL) lead as the reference. However, if the RL lead should become disconnected, the lead drive circuit 106 has a hierarchy of leads which will subsequently be selected as the driven lead. This selection may also entail switching the leads being monitored by the monitor system. For example, in a five-lead system, if the monitor system is monitoring lead II, the left arm and the right arm are being monitored and the RL lead is the driven lead. If the RL lead should fall off the patient, the monitor system detects the lead fault and switches the leads being monitored so that an intact lead may be used as the driven lead. For example, the chest lead could be driven if the RL lead has a lead fault.

The lead fault detector circuit 108 is also well known to those of skill in the art. The analog input signals 102a–g are each pulled up to a reference voltage (not shown) through a very high resistance value (not shown) within the patient interface circuitry 14 (see FIG. 1). The signals from the buffer 104 are coupled to the lead fault detector circuit 108 which uses comparators to determine if the signals from the buffer 104 are above a predetermined threshold. The threshold is selected to be below the pull-up resistor reference voltage. If the lead is properly connected to the patient, the impedance of the lead is sufficiently low that the signal from the patient will not be affected by the pull-up resistors. When a lead becomes detached from the patient, the pull-up resistors will cause the voltage on the disconnected lead to be pulled up to the reference voltage. When the voltage on the buffer output line exceeds the predetermined comparator threshold, the lead fault detector circuit 108 indicates which of the patient leads has the fault. A visual or audible alarm (not shown) informs the user of a lead fault.

The buffer 104 has a high input impedance so that it does not load down the input signals. In addition, the buffer 104 has the capacity to drive the lead summing network 112 and the analog output signal terminals 110a–g. The analog signal output terminals 110a–g are used to couple signals from one ASIC to another if the monitor system 10 (see FIG. 1) is expanded to include multiple ASICs. When multiple ASICs are used, selected signals from the analog signal output terminals 110a–g from one ASIC are coupled to selected analog expansion input terminals 114a–g on another ASIC. The interconnection of multiple ASICs will be described in detail below.

The lead summing network 112 accepts the signals from the buffer 104 and analog expansion inputs 114a–g. The lead summing network 112 produces different combinations of lead select signals that are required for the various monitor system configurations. The lead summing network 112 responds to both the lead selection signals 116 and the system configuration signals 118 to determine the manner in which the various inputs will be summed. The internal structure of the lead summing network includes a series of analog switches and differential amplifiers. There are numerous configuration for analog switches and operational amplifiers that are acceptable for the proper use of the invention. Examples of lead summing configurations are provided below. Table 1 below lists the standard positions for electrode placement on a patient for a number of different system configurations.

TABLE 1

| Standard Electrode Placement for Various ECG Configurations | |
|---|---|
| Configuration | Electrode Placement |
| Standard 3 Lead | RA, LA, RL; LL Reference |

TABLE 1-continued

| Standard Electrode Placement for Various ECG Configurations | |
|---|---|
| Configuration | Electrode Placement |
| Standard 5 Lead | LL, LA, RA, C; RL Reference |
| Standard 12 Lead | LL, LA, RA, C1, C2, C3, C4, C5, C6; RL Reference |
| Standard 15 Lead | RA, LA, LL, C1, C2, C3, C4, C5, C6, H, E, M, I; RL Reference |
| Frank Leads | A, C, E, F, I, M & H; RL Reference |
| Research Leads | Cx1, Cx2, Cx3, X1(+), X1(−), X2(+), X2(−), X3(+), X3(−), |
| Holter Leads | CH1(+), Ch1(−), CH2(+), Ch2(−), CH3(+), Ch3(−), |
| Pediatric Leads | C3R, C4R, C7, (Extra Chest Leads) |
| Late Potential Leads | X(+), X(−), Y(+), Y(−), Z(+), Z(−) |

Note that it is standard terminology to refer to the right leg as RL, right arm as RA, left arm as LA, etc. These terms are well known to those skilled in the art of ECG analysis.

The lead summing network 112 sums the various patient electrode leads described above to provide the standard ECG leads described in Table 2 below. It should be noted that several of the standard leads are not derived by simple addition and substraction of patient electrode signals. The lead summing network 112 can derive the various standard leads listed below.

TABLE 2

| Derived ECG Output Signals | |
|---|---|
| Derived Signal Output | Formula |
| I | LA − RA |
| II | LL − RA |
| III | LL − LA |
| V1 | C1 − ⅓(LA + RA + LL) |
| V2 | C2 − ⅓(LA + RA + LL) |
| V3 | C3 − ⅓(LA + RA + LL) |
| V4 | C4 − ⅓(LA + RA + LL) |
| V5 | C5 − ⅓(LA + RA + LL) |
| V6 | C6 − ⅓(LA + RA + LL) |
| $X_{FRANK}$ | 0.610A + 0.171C − 0.781I |
| $Y_{FRANK}$ | 0.655F + 0.335M − 1.000H |
| $Z_{FRANK}$ | 0.133A + 0.736M − 0.374E − 0.231C |
| VX1 | Cx1 − ⅓(LA + RA + LL) |
| VX2 | Cx2 − ⅓(LA + RA + LL) |
| VX3 | Cx3 − ⅓(LA + RA + LL) |
| X1 | X1(+)-X1(−) |
| X2 | X2(+)-X2(−) |
| V3R | C3R − ⅓(LA + RA + LL) |
| V4R | C4R − ⅓(LA + RA + LL) |
| V7 | C7 − ⅓(LA + RA + LL) |
| Ch1 | Ch1(+) − Ch1(−) |
| CH2 | CH2(+) − Ch2(−) |
| Ch3 | CH3(+) − Ch3(−) |
| $X_{LP}$ | X(+) − X(−) |
| $Y_{LP}$ | Y(+) − Y(−) |
| $Z_{LP}$ | Z(+) − Z(−) |

All the leads described above are derived within the lead summing network 112. However, the monitor system 10 (See FIG. 1) also derives other leads in software. The augmented leads, $aV_R$, $aV_L$, and $aV_F$ are derived by simple addition and substraction of other leads derived by the lead summing network 112. The augmented leads are derived using the formulas in Table 3 below.

TABLE 3

| Augmented Lead Formulas |
|---|
| $aV_R = -\frac{1}{2}(I + II) = RA - \frac{1}{2}(LA + LL)$ |
| $aV_L = \frac{1}{2}(I - III) = LA - \frac{1}{2}(LL + RA)$ |
| $aV_F = \frac{1}{2}(II + III) = LL - \frac{1}{2}(LA + RA)$ |

As stated above, the augmented are derived in software in the presently preferred embodiment. However, in an alternative embodiment, the augmented leads could be derived in the lead summing network 112 by adding more differential amplifiers and resistors.

As noted above, some of the leads, such as the X, Y, and Z leads are mathematically derived within the lead summing network 112. These leads are derived using laser trimmed precision resistors with the differential amplifiers to provide the correct values for the voltage contribution for each patient electrode. In the presently preferred embodiment, the laser trimmed precision resistors are external to the ASIC 100 for decreased cost. The external resistors are coupled to the appropriate differential amplifiers through the analog signal output terminals 110a-g, analog expansion inputs 114a-g, and the lead selection outputs 120a-f. Alternatively, the laser trimmed precision resistors may be physically located within the ASIC 100. The various derived signal outputs are used in different lead configurations, and not all leads are available for all electrode placements. The standard lead configurations are indicated in Table 4 below.

TABLE 4

| Standard Lead Configurations | |
|---|---|
| Configurations | Available Leads |
| Standard 3 Lead | I, II, III |
| Standard 5 Lead | I, II, III, and V, where V is any one of V1 through V6 |
| Standard 12 Lead | I, II, III, V1, V2, V3, V4, V5, V6, VA, VB, VC, X1, X2 |
| Standard 15 Lead | I, II, III, V1, V2, V3, V4, V5, V6, X, Y, Z, Vx1, Vx2, Vx3, X1, X2, X3, V4R, V7, Ch1, Ch2, Ch3 |
| Frank Leads | X, Y, Z |
| Holter Leads | Ch1, Ch2, Ch3 |
| Late Potential Leads | $X_{LP}$, $Y_{LP}$, $Z_{LP}$ |

An an example of the operation of the lead summing network 112, assume that there is a single ASIC 100 in an ECG monitor system 10 (see FIG. 1). With a single ASIC, the monitor system can operate in a three-lead, five-lead, or Holter monitor mode. In a standard three-lead configuration, the RA, LA, and LL electrodes are coupled to the monitor system 10. The RA, LA, and LL leads are coupled to the ASIC analog signal inputs 102a-c, respectively. The lead summing network 112 receives these signals from the buffer 104 and derives the standard leads described in Table 4 above.

Figure 3:
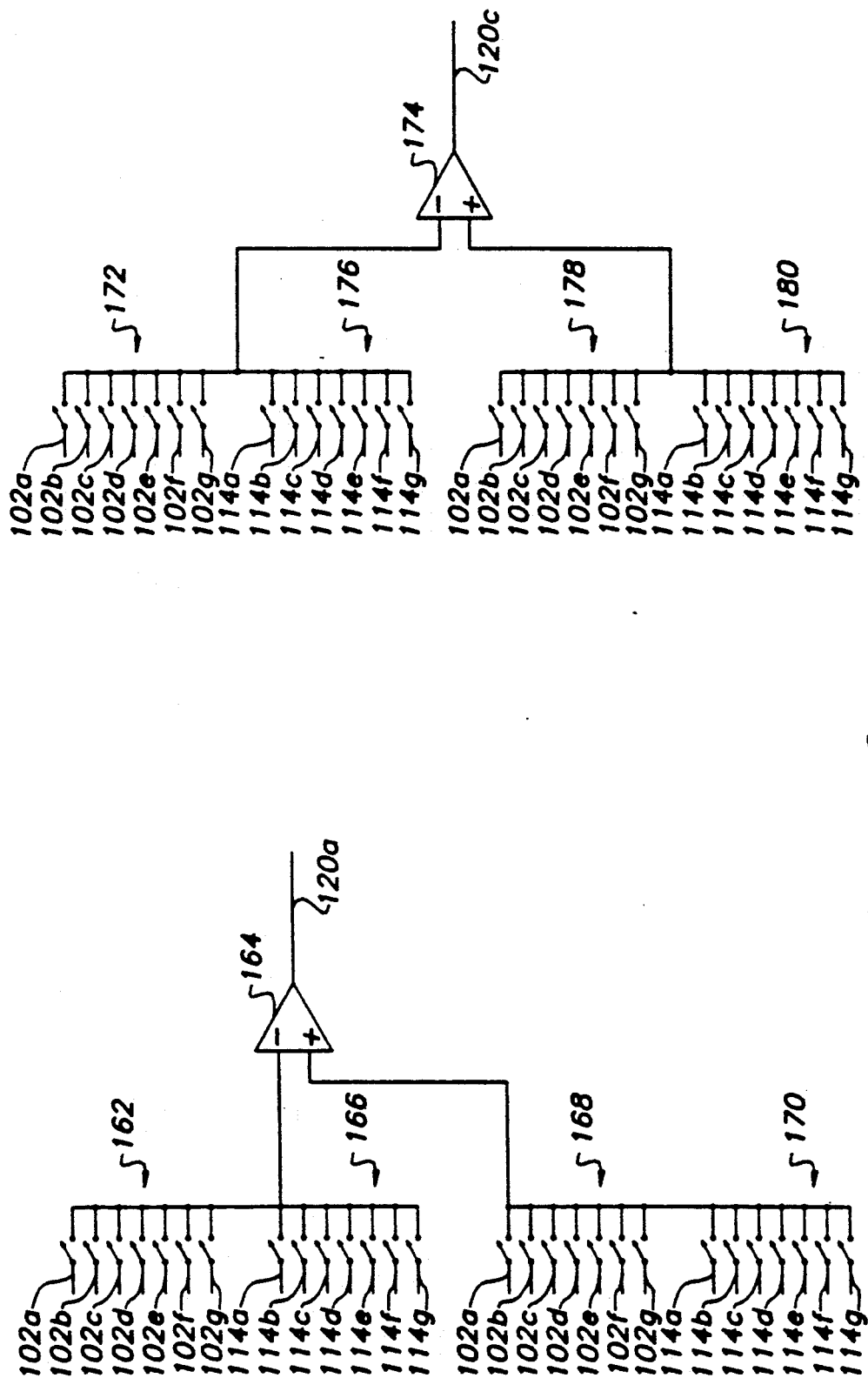
FIG. 3 is a functional block diagram of one embodiment of the lead summing network.
Figure 4:
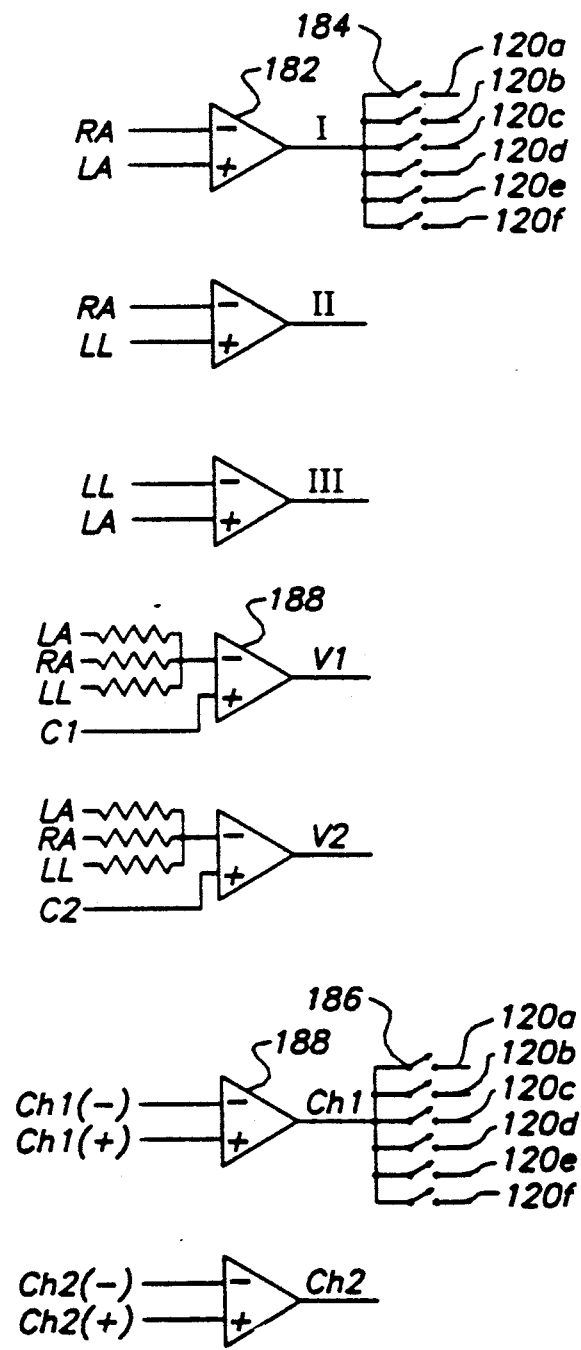
FIG. 4 is a functional block diagram of another embodiment of the lead summing network.

Two possible embodiments of the lead summing network 112 are shown in FIGS. 3 and 4. The block diagrams are intended only to provide examples of the type of structure found in the lead summing network 112. For the sake of clarity, not all analog switches and differential amplifiers are shown. Most resistors have also been omitted for the sake of clarity. Those skilled in the art will recognize that there are many possible configurations for using a differential amplifier and the placement of resistors and the actual values of resistors will vary from one configuration to another. In some cases where analog signals are summed, such as the V1-V6 leads, resistors are shown, but the resistance values are omitted. As previously stated, the precision resistors in the presently preferred embodiment are external to the ASIC 100 (see FIG. 2). It should be recognized that the block diagrams of FIGS. 3 and 4 are representational of the many possible circuit configurations that may be used satisfactorily in the inventive ASIC.

As an example of lead summing, the analog switches 162 in FIG. 3 couple each of the analog signals from the buffer 104 to the negative input of the differential amplifier 164. A set of analog switches 166 couple each of the analog signals from the analog expansion inputs 120a-g to the negative input of the differential amplifier 164. Similarly, a set of analog switches 168 couple each of the analog signals from the buffer 104 to the positive input of the differential amplifiers 164 while the analog switches 170 couple the analog signals from the analog expansion inputs 120a-g to the positive input of the differential amplifier 164. To derive lead I, for example, from the differential amplifier 164, the lead selection signals 116 (see FIG. 2) close the switch coupling the RA electrode in analog switch 162 to the negative input of differential amplifier 164, while also closing the switch to couple the LA electrode in analog switch 168 to the positive input of differential amplifier 164. Other leads are derived in a similar manner. For example, lead III is derived by closing the switches in analog switches 172 and 178 to couple the LA and LL leads to the negative and positive inputs, respectively, on differential amplifier 174. If the ASIC 100 (see FIG. 2) were configured for Holter operation, the analog switches 162 and 168 would couple the Ch1(+) and the Ch1(−) electrodes to the appropriate inputs for differential amplifier 164. The configuration shown in FIG. 3 minimizes the number of differential amplifers required, but increases the number of analog switches required. This arrangement requires six differential amplifiers (one for each lead selection output 120a-f) and requires 168 analog switches to provide all possible combinations of inputs. As is known in the art, analog switches require a larger amount of space on an integrated circuit than differential amplifiers.

Therefore, an alternative embodiment for the lead summing network is shown in FIG. 4. In this embodiment there is a differential amplifier for each possible lead configuration. The outputs from each of the differential amplifiers are coupled to a switch for each of the lead selection outputs 120a-g. Lead I is derived by coupling the LA and RA electrodes from the buffer 104 to the positive and negative inputs, respectively, on differentiated amplifier 176. Other leads are derived in similar fashion by other differential amplifiers. If it is desired to couple lead I to the first lead selection output 120a, the switch 184 would close to connect lead I to the first lead selection output 120a. Any of the derived leads can be coupled to any of the lead selection outputs 120a-g in a similar fashion. If the ASIC 100 (see FIG. 2) were configured for Holter operation, the analog switch 186 would couple the Ch1 lead from differential amplifier 188 to the lead selection output 120a. The lead summing configuration shown in FIG. 4 minimizes the number of analog switches, but increases the number of differential amplifiers and the number of precision resistors required for the lead summing network 112. The embodiment of FIG. 4 requires 17 differential amplifiers and 102 analog switches. As discussed above, there are a number of alternate configurations for the lead summing network 112 that may be used satisfactorily. The examples of lead summing network configurations shown in FIGS. 3 and 4 represent only two of the many possible configurations. Alternatively, a combination of the configuration shown in FIGS. 3 and 4 may be used to optimize the number of differential amplifiers and the number of precision resistors versus the amount of physical space required for analog switches. Also, there may be applications in which all possible combinations of lead summing are not required. In that event, still other possible lead configurations are possible.

As an example of V lead derivation, if the ASIC is used with a five-lead ECG monitor system, the RL, LA, LL, and C1 electrodes are coupled to the monitor system 10. The RA, LA, LL, and C1 analog signals are coupled to the ASIC analog signal inputs 102a–d, respectively. If the lead summing network 112 were configured as shown in FIG. 4, the first three output signals from the lead summing network 112 are derived as described above for the three-lead configuration.

The V1 lead is derived in the lead summing network 112 by coupling the LA, RA and LL signals to a differential amplifier 188 through precision resistors to produce the summed signal ⅓(LA+RA+LL). The summed signal is coupled to the negative input of the differential amplifier 188, while the C1 lead is coupled to the positive input of differential amplifiers 182. An analog switch (not shown) couples the V1 lead to the selected lead selection output 120a–g. Other V leads are derived in a similar manner.

The system configuration signals 118 control the configuration of lead summing within the lead summing network 112. One of the system configuration signals 118 selects between standard lead configuration and Holter configuration. In a standard lead configuration, the electrodes are unipolar and are coupled to differential amplifiers to derive the various leads such as lead I (LA-RA). If the Holter configuration is selected, the electrodes are in a bipolar configuration (e.g., Ch1(+) and Ch1(−)) and the bipolar electrode inputs are coupled to a differential amplifier within the lead summing network 112 to provide the appropriate bipolar signals (e.g., Ch1(+)-Ch1(−)). The ASIC 100 is capable of operating in either mode depending on the logic level on one of the lead configuration signals 118. The other lead configuration signal 118 determines whether the lead summing network 112 will use extra analog signal inputs 102a–g to derive extra chest leads or an extra bipolar pair of signal inputs.

Referring again to FIG. 2, the lead selection outputs 120a–f are coupled to a pacer detect circuit 122 and a pacer delay network 130. The pacer detect circuit 122 detects both normal heart pacemaker signals and shorter bioimpedance pulses often found in demand pacemakers. As explained above, pacer signals are typically much larger in amplitude than ECG signals and will saturate ECG amplifiers if they are not eliminated. The two different types of pacer pulses are blanked for different lengths of time because the different pacer pulses have different durations. Therefore, the pacer detect circuit 122 responds to the pacer detect lead select control lines 124 and detects the pacer pulse. The pacer detect outputs 126 provide an indication of the type of pacer signal (i.e., typical pacer signal or bioimpedance signal). The pacer detect circuit 122 also provides a positive and negative peak amplitude output signals 128, to allow analysis of the pacer waveform itself. The controller 24 (see FIG. 1) receives the pacer detect outputs 126 and determines which type of pacer signal is present so that the lead selection output signals 120a–f can be blanked (i.e., switched off) before reaching the programmable bandpass filters 136 and programmable amplifiers 144. A detailed description of the pacer detect circuit 122 is provided below.

The lead selection signals 120a–f are also coupled to the pacer delay network 130 which delays the analog signal a sufficient length of time so that the pacer detect circuit 122 can detect and analyze the pacer signal. The pacer delay network 130 comprises a linear phase Bessel lowpass filter with a cutoff frequency of approximately 500 Hertz. This will delay the analog signals from the lead selection signals 120a–f for approximately two milliseconds.

The analog signals from the pacer delay network 130 are coupled to a pacer blanking network 132, which is controlled by a pacer blanking control line 134. The pacer blanking network 132 comprises a series of analog switches which are normally closed, but will open when activated by the pacer blanking control line 134. Thus, the analog signals are normally passed to a programmable bandpass filter 136, but are disconnected from the programmable bandpass filter network 136 when the signals are blanked.

The programmable bandpass filter network 136 provides individually programmable bandpass filters for each of the analog signals of the lead selection signals 120a–f. The input to each of the individual filter channels has a capacitor (not shown) placed in series with each input to block DC signals and to hold the filter input at a constant level in the event that the input to the filters are blanked. This capacitor is part of a highpass filter portion of the bandpass filter 136. When the pacer blanking circuit 132 opens the analog switches, the capacitor holds the filter input at a substantially constant level during the blanking period. The bandpass filter programming lines 138 control the settings for the individual bandpass filters. The highpass filter section of the bandpass filter 136 has a set cutoff frequency of 0.05 Hertz (Hz) and is not programmable. The cutoff frequency for the lowpass filter section of the bandpass filter network 136 is programmable from 40 Hz to 500 Hz. The 500 Hz cutoff frequency allows for the analysis of late potentials often used in ECG diagnostic analysis. As is well known, a highpass filter with a very low cutoff frequency requires a relatively large capacitance value in the filter, resulting in a long time constant for the filter.

Because the highpass filter has a long time constant (approximately 20 seconds), the ASIC 100 has a trace recovery circuit 140 to actively restore the baseline of any signal channel. The baseline of a signal is the DC component of the analog signal. The DC component drastically shifts in the event of a disconnected lead, a defibrillator pulse, or the like. The shift of the DC component causes a temporary signal overload, but the recovery period can be 20 seconds or more due to the long time constant of the highpass filter. If the controller 24 (see FIG. 1) determines that a signal has saturated at one of the power supply rails for more than 20 milliseconds, the ASIC 100 will discharge the capacitor in the highpass filter portion of the bandpass filter circuit 136 for the particular channel that has overloaded. The discharge of the capacitor in the highpass filter portion will shorten the time constant of the highpass filter and restore the signal baseline in a short period of time.

Similarly, the controller 24 (see FIG. 1) monitors the baseline drift of the inputs to the bandpass filter 136. If the drift becomes too large and the AC signal nears the dynamic range of the ASIC 100, the trace recovery circuit 140 will discharge the capacitor in the highpass filter portion of the bandpass filter 136 as described above before the signal causes an overload. This type of baseline restoration may correct for some artifact such as motion artifact. The trace recovery control lines 142 determine which channel will have its baseline restored.

The filtered signals from the bandpass filter network 136 are coupled to the programmable amplifier network 144. The programmable amplifier network 144 of the presently preferred embodiment comprises individual programmable gain amplifiers for each of the analog channels. The gain of each amplifier is individually programmable via the programmable amplifier network control lines 146. The gain range for the individual amplifiers ranges from 10 to 1000.

The outputs from the programmable amplifier network 146 are coupled to amplified analog output terminals 148a-f. The outputs from the programmable amplifier network 146 are also coupled as inputs to the analog multiplexor 150. The analog multiplexor 150 of the presently preferred embodiment has eight inputs, six of which are the processed analog signals from the lead selection outputs 120a-f of the lead summing network 112. The other two inputs to the analog multiplexor 150 are the plus and minus peak amplitude signals 128 from the pacer detect circuit 122. The same lead selection signals 116 that control the lead summing network 112 are also control lines to the analog multiplexor 150. The lead selection control lines 116 select one of the eight input signals to couple to a single output line from the analog multiplexor 150.

The selected output from the analog multiplexor 150 is coupled to the input of a sample/hold circuit 154, which is controlled by a sample/hold control line 156. The sample/hold circuit 154 operates in a manner well known to those of skill in the art and will not be described herein. The output of the sample/hold circuit 154 is coupled to an output terminal 158 as an output from the ASIC 100. As previously discussed, the presently preferred embodiment does not contain an ADC. This allows the user a greater degree of flexibility in selecting and ADC closely matched with the particular needs. In an alternative embodiment, an ADC may be incorporated into the ASIC 100 and the output 158 of the sample/hold circuit 154 would be coupled to the analog input of the ADC.

Power is supplied to the ASIC 100 through a plurality of power supply terminals 160. In one embodiment of the invention, the ASIC 100 is powered by a single +5 VDC power supply, as would be useful for battery powered operation. In other applications, the ASIC 100 is powered by a +/−5 VDC power supply. The presently preferred embodiment has two ground systems, an analog ground system and a digital ground system to prevent switching noise from the digital ground from causing noise in the analog portions of the ASIC 100.

Figure 5:
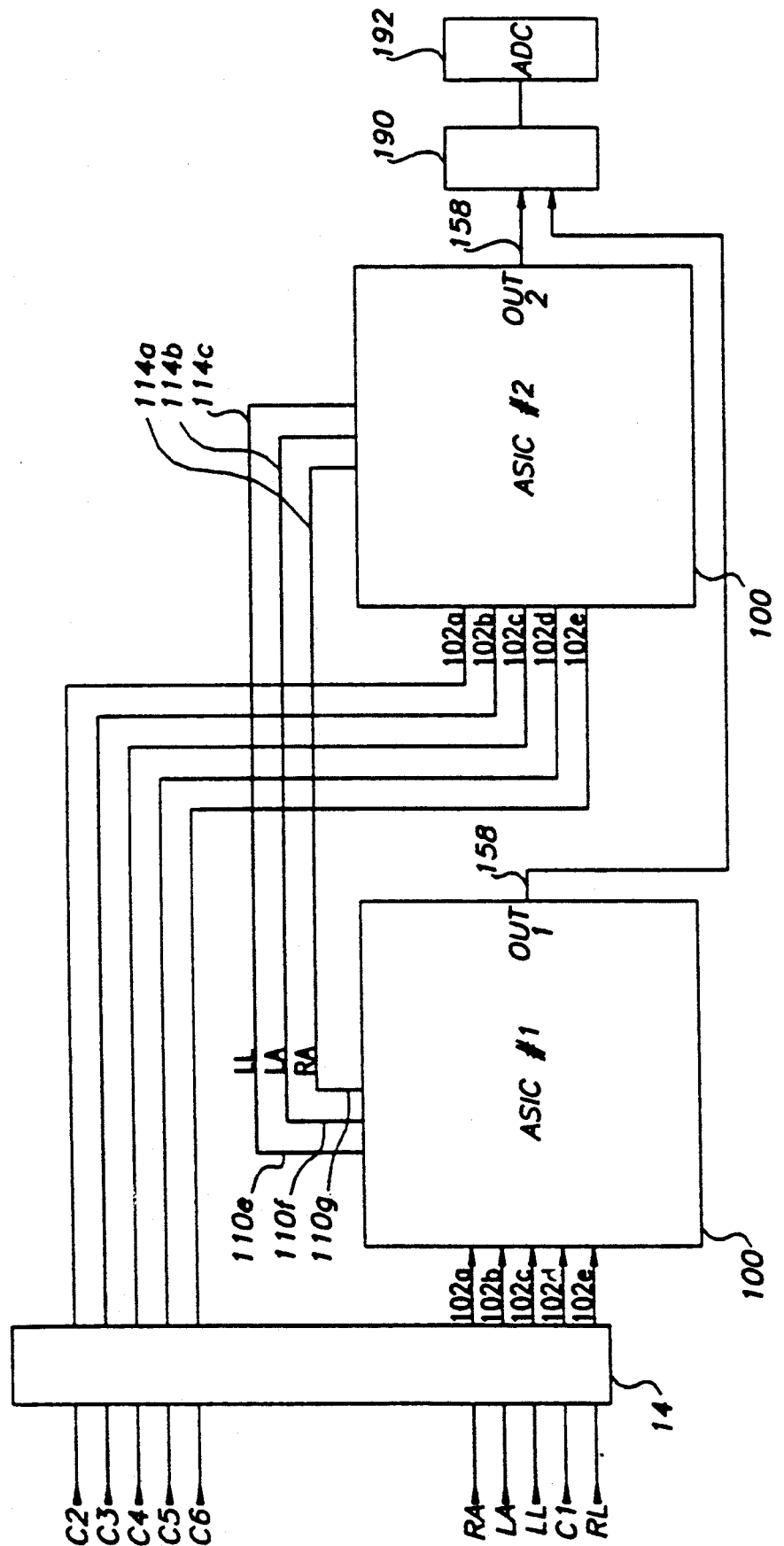
FIG. 5 shows two of the integrated circuits of FIG. 2 coupled together to provide expanded signal monitoring capability.

The system architecture of the present invention is flexible enough to allow virtually any number of ASICs 100 to be connected within a single monitor system 10 (see FIG. 1). For example, a 12-lead ECG monitoring system, shown in FIG. 5, comprises two individual ASIC chips, previously described. The internal components of each individual ASIC have been omitted for clarity. In the example shown in FIG. 5, several of the analog input leads from each ASIC are coupled to the patient through the patient interface circuitry 14. In addition, several of the analog signal output terminals 110a-g from ASIC #1 are coupled to the analog expansion inputs 114a-g of ASIC #2, thus enabling the combination of two ASICs to produce all standard lead configurations derived from a 12-lead ECG system as shown in Table 4. Specifically, ASIC #1 uses the RA, LA, LL, C1, and RL electrode signals from the patient interface circuit 14 to produce the I, II, III, V1, VA, and VB leads. The VA and VB leads are extra chest leads that are derived if the system configuration signals 118 are selected to have standard configuration (as opposed to Holter configuration) and extra chest leads (as opposed to an extra pair of bipolar leads). If the user had configured the ASIC 100 for an extra pair of bipolar leads, there would be no VA and VB outputs from the lead summing network. In place of the VA lead, there would be an X1 lead.

The inputs from the patient interface circuit 14 to the lead summing network 112 on ASIC #2 are V2, V3, V4, V5, V6, and VC. If ASIC #2 were configured for an extra pair of bipolar leads instead of extra unipolar chest leads, the VC lead would be replaced with the X2 lead. Each of the two ASICs has its own sample/hold circuit 154 (see FIG. 2). The outputs of the two ASICs are coupled through an external analog multiplexor 190 to an external ADC 192. The monitor system 10 (see FIG. 1) may also monitor additional analog voltages with the external analog multiplexor 190. For example, the monitor system 10 may monitor power supply voltages or a respiration signal from an external respiration monitor circuit (not shown).

Figure 6:
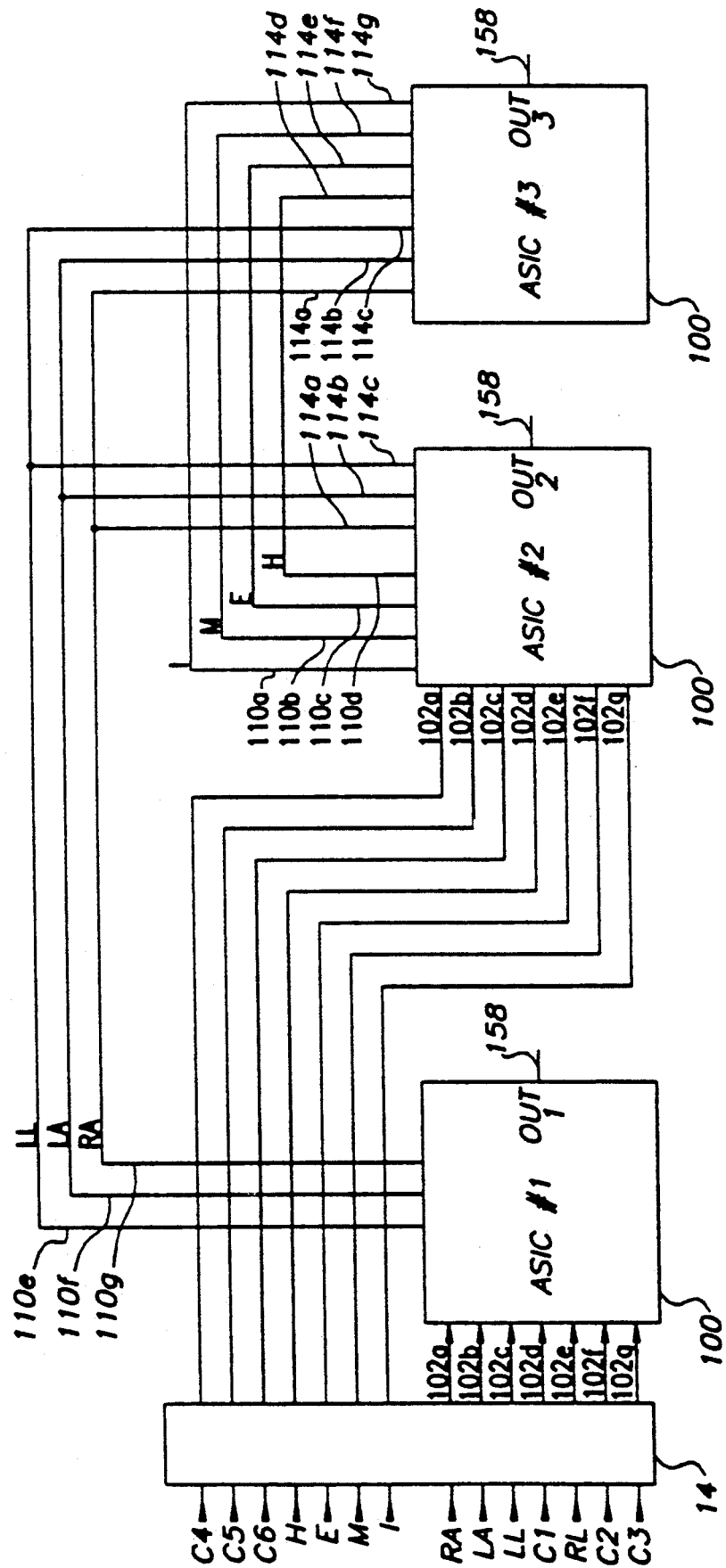
FIG. 6 shows three of the integrated circuits of FIG. 2 coupled together to provide expanded signal monitoring capability.

In similar fashion, three or more individual ASICs may be coupled together using a combination of analog signal inputs, analog signal outputs, and analog expansion inputs to couple various combinations of patient electrodes to the various ASICs. For example, a 15-lead ECG monitoring system could be constructed using three individual ASICs as shown in FIG. 6. The internal components of each individual ASIC have also been omitted from FIG. 6 for clarity. In the 15-lead configuration, the RA, LA, LL, C1, RL, C2, and C3 electrodes are coupled from the patient interface circuit 14 to the analog signal inputs 102a-g, respectively for ASIC #1. Thus, ASIC #1 produces leads I, II, III, V1, V2, and V3. Patient electrodes C4, C5, C6, H, E, M, and I are coupled from the patient interface circuit 14 to the analog signal inputs 102a-g for ASIC #2. In addition, the LL, LA and RA electrode signals are coupled from the analog signal output terminals 110e-g on ASIC #1 to the analog expansion inputs 114a-c, respectively, on ASIC #2. Thus, ASIC #2 produces leads V4, V5, V6, X, Y, and Z.

The third ASIC in the 15-lead monitor system, ASIC #3, is not directly coupled to the patient, but receives all its analog inputs from ASIC #1 and ASIC #2 through the analog expansion inputs 114a-g on ASIC #3. The RA, LA and LL electrode signals are coupled from the analog signal output terminals 110e-g on ASIC #1 to the analog expansion inputs 114a-c, respectively, on ASIC #3. In addition, the H, E, M and I electrode signals are coupled from the analog signal output terminals 110a-d on ASIC #2 to the analog expansion inputs 114d-g, respectively, on ASIC #3. ASIC #3 uses these signals to derive the leads X1, X2, Vx1, Vx2, and Vx3. Again it should be noted that in the above example, the ASICs 100 have system configuration signals 118 that are set to provide standard configuration (as opposed to Holter configuration) and extra unipolar leads (as opposed to an extra pair of bipolar leads).

Each of the three ASICs 100 contains a sample/hold circuit 154 (see FIG. 2). The sample/hold output 158 of each ASIC is coupled through an external analog multiplexor (not shown) to an external ADC (not shown). In similar fashion, additional ASICs may be incorporated into the monitor system 10 (see FIG. 1). By using the combination of analog signal inputs 102a-g, analog signal output terminals 110a-g, and the analog expansion inputs 114a-g, a wide variety of physiological signals may be derived.

While the examples described above all relate to ECG monitoring, the system architecture of the present invention is also applicable to other physiological signal processing systems, such as diagnostic EEG monitoring, auditory brain stem response (ABR) monitoring, or the like. For example, a single ASIC device using the system architecture of the present invention could be utilized for ABR monitoring. For more sophisticated EEG monitoring, such as brain-mapping, two or more ASICs may be coupled in a manner as described above to produce the desired number of EEG channels.

The system architecture of the present invention overcomes the problems of the prior architecture by allowing flexibility in system design using virtually any number of individual ASICs which may be connected in an unlimited number of configurations.

The ASICs may be interconnected by a variety of techniques. For example, a printed circuit board could be designed to accommodate a variable number of individual ASICs. As ASICs are added to the printed circuit board, their respective analog signal inputs, analog signal output terminals and analog expansion inputs are connected together in a predetermined fashion by virtue of the printed circuit board layout. Alternatively, the analog signal inputs, analog signal output terminals, and analog expansion inputs could be coupled on a printed circuit board to a set of signal jumpers. By selecting the appropriate jumpers, the user may interconnect the system in any desired fashion. This approach offers greater flexibility over the printed-circuit hardwired approach, since circuit configuration could be easily changed.

The integration of many functions onto a single ASIC also solves another problem that frequently occurs in physiological monitors. As previously mentioned, RFI from sources such as electrosurgical equipment often interferes with the proper operation of physiological monitors. Such RFI is often radiated directly into equipment or inductively coupled to AC power lines and capacitively coupled to the circuit ground of the physiological monitor. Well known techniques such as RFI shielding and minimizing lead length may be used to reduce the amount of radiated RFI. The ASIC 100 of the present invention is designed to incorporate many features that typically require external circuitry and, thus, additional space on a printed circuit board. The extra printed circuit board increases capacitance to the AC power line. The ASIC 100 incorporates many circuits into a single integrated circuit, thus reducing the capacitance. Furthermore, the ASIC 100 is designed so as to minimize the circuit ground and reduce the capacitive coupling to the AC power lines.

Another inventive aspect of the ASIC 100 is the pacer detect circuit 122. As previously stated, there are different types of heart pacemaker signals. The pacer detect circuit is capable of detecting both the normal pacer signal and the shorter bioimpedance pulse. In addition to detecting the pulse width, the pacer detect circuit 122 can also determine the polarity and amplitude of the pacer pulse.

A typical pacemaker pulse ranges from approximately +/−1 millivolt to +/−700 millivolts in amplitude. The duration of the pacer pulse may range from 0.1 milliseconds to 2 milliseconds, with a typical rise/fall time of 100 microseconds maximum. In contrast, the bioimpedance pulse from the newer demand pacemakers is often a current pulse of +/−1 milliampere which can result in a signal with an amplitude ranging from +/−5 millivolts to +/−700 millivolts. Bioimpedance pulses are much shorter in duration than a typical pacer pulse and may range from approximately 2 microseconds to 100 microseconds in duration. The pacer detect circuit 122 of the ASIC 100 is capable of detecting and distinguishing between the different types of pacer pulses.

The pacer detect circuit 122 uses filters and digital timing techniques to eliminate unwanted signals and to distinguish between the different types of pacemaker pulses. The ECG signal is an unwanted signal for purposes of pacer detection. The ECG signal is usually band limited to approximately 125 Hz, but diagnostic ECG monitor systems may have a bandwidth up to 500 Hz. The pacer detect circuit 122 eliminates the ECG signal so that it does not interfere with the proper detection of pacer signals.

Monitor systems 10 (see FIG. 1) often include respiration monitoring circuitry (not shown) that applies a high frequency signal to some of the patient's electrodes and measures the impedance between the electrodes. There is a slight change in impedance as the patient breathes. This impedance change can be detected and used to monitor the respiration. Before the use of bioimpedance pulses, systems of the prior art could separate the ECG signal and the respiration signal by lowpass filtering the ECG signal and highpass filtering the respiration signal. The introduction of the demand pacemaker, which uses bioimpedance pulses, creates problems for the prior art systems. Most prior art system were not designed to detect bioimpedance pulses. Simply adding a circuit to detect short pulses will not solve the problem because the bioimpedance pulse bandwidth overlaps the range of frequencies typically used by the respiration detection circuit.

In one monitor system, for example, a sine wave of approximately 62.5 kilohertz is used to monitor the patient's respiration. This signal must be removed before the pacer detection circuit 122 will operate satisfactorily. As shown in FIG. 2, the lead selection signals 116a-f from the lead summing network are coupled to the pacer detect circuit 122. The control lines 124 select which leads are used for pacer detection. The operation of the pacer detect circuit is best seen in the block diagram of FIG. 7. The lead selection outputs 120a-f are coupled to the pacer detect circuit 122 through a multiplexor 202 which selects which lead will be monitored for the pacer pulse signals. The channel selection is controlled by pacer detect lead select control lines 124. The channel may be manually selected by the user or automatically depending on which leads are being monitored by the monitor system 10 (see FIG. 1). The monitor system 10 also has automatic switching similar to that described in the lead fault circuit 108 (see FIG. 2). If the lead fault circuit 108 detects a lead fault in a lead that is used by the pacer detect circuit 122, the monitor system 10 will automatically switch to an intact lead so that the pacer detect circuit 122 will continue to operate.

The selected lead is coupled by the multiplexor 202 to a lowpass filter 204 to remove any interfering signals such as a respiration signal or the horizontal sync pulses from a television. To effectively remove these signals, the presently preferred embodiment of the ASIC 100 (see FIG. 2) uses a six pole filter with a cutoff frequency of approximately 10 kilohertz. The output of the lowpass filter 204 is coupled to a highpass filter 206, which also differentiates the signal. The highpass filter has a single zero and a cutoff frequency of approximately 3.3 kilohertz. The highpass filter removes the unwanted ECG signal. The highpass filter 206 also differentiates the signal to produce two pulses corresponding to the rising and falling edges of the pacer pulse. It should be noted that a pacer pulse may be positive, negative, or bipolar. The pacer detect circuit 122 is able to detect any pulse within the parameters specified above. If the pulse is a positive going pulse, the differentiator 206 will produce a positive pulse on the rising edge of the pacer pulse, and a negative pulse on the falling edge of the pacer pulse. Conversely, if the pacer pulse is a negative pulse, the differentiator 206 will produce a negative pulse corresponding to the falling edge of the pacer pulse and a positive pulse corresponding to the rising edge of the pacer pulse. Similarly, if the signal is bipolar, the differentiator will produce a positive pulse corresponding to the leading edge of the pacer pulse if the leading edge is positive, or a negative pulse if the leading edge of the pacer pulse is negative.

Figure 7:
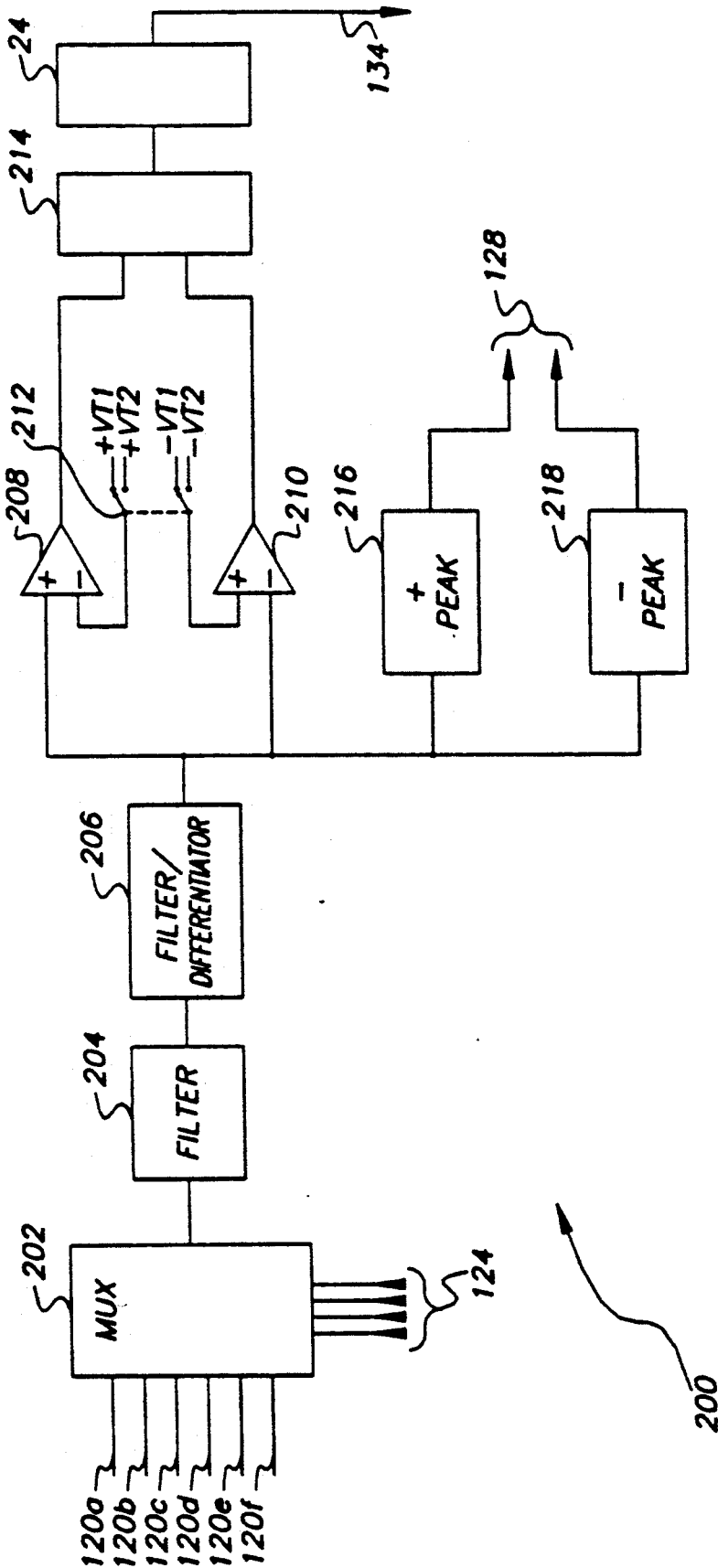
FIG. 7 is a functional block diagram of the pacer detect circuit.

The output of the highpass filter and differentiator 206 is coupled to a pair of comparators 208 and 210. Comparator 208 detects the positive going pulse from the differentiator and generates a digital logic compatible signal whenever the differentiator generates a positive pulse that exceeds the comparator threshold. The pacer detect circuit 122 uses two thresholds. The primary threshold is one millivolt and is used in normal operation with adults. In an environment where a large amount of motion artifact is present, as when a neonate is monitored, the user may select the secondary threshold of ten millivolts. A switch 212 selects the threshold. The switch may be manual or automatic in operation. Whenever, the positive pulse from the differentiator 206 exceeds the selected threshold, the comparator 208 generates a logic compatible pulse. Similarly, the comparator 210 detects negative pulses from the differentiator 206. Whenever the negative pulse from the differentiator 206 is less than the selected negative threshold, the comparator 210 generates a digital logic compatible pulse. As with the comparator 208, there are two alternate thresholds that may be used with the comparator 210. The outputs from the comparators 208 and 210 are the pacer detect outputs 126 (see FIG. 2). As a person of ordinary skill in the art will recognize, there are many possible configurations for the comparators 208 and 210. The circuit shown in FIG. 7 is only one example of the may possible configurations.

The controller 24 (see FIG. 1) monitors the pacer detect outputs 126 (see FIG. 2), and starts a timer 214 when either of the outputs changes states. The timer 214 stops counting when the other of the pacer detect outputs changes states. Thus, the timer 214 measures the elapsed time between the pulses from the comparators 208 and 210. The controller 24 monitors both of the pacer detect outputs and will, therefore, detect pacer pulses of either polarity or bipolar pulses. The controller can determine the polarity of the pacer pulse by determining which of the comparators 208 and 210 first exceeded the selected threshold. For example, comparator 210 will change states first if the pacer pulse is negative (or bipolar with a negative leading edge). Conversely, comparator 208 will change states first if the pacer pulse is positive (or bipolar with a positive leading edge).

The controller 24 (see FIG. 1) can determine the type of pacer pulse by determining the elapsed time from the timer 214. If the elapsed time is between 2 microseconds and 100 microseconds, the pacer pulse is a bioimpedance pulse. In that event, the controller 24 uses the pacer blanking control line 134 (see FIG. 2) to blank the ECG signal for 2 milliseconds. On the other hand, if the elapsed time from the timer 214 is between 0.1 milliseconds to 2 milliseconds, the controller 24 uses the pacer blanking control line 134 (see FIG. 2) to blank the ECG signal for 20 milliseconds. Thus, the ASIC 100 will blank the ECG signal for different lengths of time depending on the type of pacer pulse detected by the pacer detect circuit 122.

The pacer detect circuit also detects the positive and negative peak amplitudes of the pacer pulse. As shown in FIG. 7, the pacer detect circuit 122 has a positive peak amplitude hold circuit 216 and a negative peak amplitude hold circuit 218. The outputs of the positive and negative peak detect circuit are the peak amplitude signals 128 (see FIG. 2) and are coupled to the analog multiplexor 150 (see FIG. 2). In this manner, the pacer pulse signal itself may be analyzed. The actual circuitry used to detect and hold a peak signal is well known to those skilled in the art and will not be discussed in detail herein. The positive and negative peak amplitude hold circuits 216 and 218 operate in essentially identical manner. The peak signal voltage is stored temporarily on a hold capacitor (not shown). If the user is monitoring the peak amplitude signals 128 (see FIG. 2), the peak amplitude signal is selected by the analog multiplexor 150 and periodically converted by the ADC (not shown). The duty cycle of the pacer pulse signals is very low because the pulses are narrow (2 microseconds to 2 milliseconds) in comparison to the repetition rate (maximum heart rate of approximately 250 beats per minute). The capacitor time constant is chosen so that the voltage on the hold capacitor will discharge before the next pacer pulse occurs. This circuit can measure the positive and negative peaks of the pacer pulse with approximately 5% accuracy.

It is to be understood that even though numerous embodiments and advantages of the present invention have been set forth in the foregoing description, the above disclosure is illustrative only, and changes may be made in detail yet remain within the broad principles of the invention. Therefore, the present invention is to be limited only by the appended claims.

I claim:

1. An application specific integrated circuit for monitoring multi-lead physiological signals from a patient, the integrated circuit comprising:

a plurality of analog input signal terminals, at least some of said plurality of input signal terminals being adapted for coupling to the patient for receiving input signals from the patient;

a plurality of analog output signal terminals coupled to at least some of said plurality of analog input signal terminals and allowing said input signals to be coupled to an external circuit;

a plurality of analog expansion input signal terminals for inputting analog signals from external analog sources;

a plurality of digital control input signal terminals responsive to a plurality of digital control signals for selecting a number of said plurality of analog signals from either said analog input signal terminals, said analog expansion input signal terminals, or a combination of both; and a lead summing network, responsive to said plurality of digital control signals, for adding said selected number of analog input signals and for outputting a set of summed output signals, whereby a set of digital control data bits on said digital control signals selects a combination of analog signals from said analog input signal terminals and analog expansion input signal terminals for processing.

2. The integrated circuit of claim 1 wherein said plurality of analog output signal terminals are coupled to at least some of said plurality of analog input signal terminals through a buffer circuit having a plurality of inputs and outputs, at least some of said plurality of analog input signal terminals coupled to said buffer circuit inputs, and at least some of said plurality of analog output signal terminals being coupled to said buffer circuit outputs.

3. The integrated circuit of claim 1, further comprising a plurality of analog filters for receiving said summed output signals and for filtering said summed output signals to provide a set of filtered signals.

4. The integrated circuit of claim 3 wherein said plurality of analog filters have a plurality of cutoff frequency settings that are individually programmable for each of said plurality of analog filters.

5. The integrated circuit of claim 3, further comprising a plurality of analog amplifiers for receiving and amplifying said set of filtered signals and for outputting a set of amplified signals.

6. The integrated circuit of claim 5 wherein said plurality of analog amplifiers have a plurality of gain settings that are individually programmable for each of said plurality of amplifiers.

7. The integrated circuit of claim 5, further comprising an analog multiplexor with a plurality of analog inputs receiving said set of amplified signals and for selecting and coupling one of said amplified signals as a multiplexor output; and a sample and hold circuit coupled to said multiplexor output to receive said selected one of said amplified signals and, under control of a hold control input, holding the signal level of said selected one of said amplified signals at a substantially constant level.

8. An ECG application specific integrated circuit for monitoring multi-lead ECG signals from a patient, the integrated circuit comprising:

a plurality of analog input signal terminals, at least some of said plurality of input signal terminals being adapted for coupling to a plurality of patient electrodes for receiving ECG input signals from said patient electrodes;

a plurality of analog output signal terminals coupled to at least some of said plurality of analog input signal terminals and allowing said ECG input signals to be coupled to an external circuit;

a plurality of analog expansion input signal terminals for inputting analog signals from external analog sources;

a plurality of digital control input signal terminals responsive to a plurality of digital control signals for selecting a number of said plurality of analog signals from either said analog input signal terminals, said analog expansion input signal terminals, or a combination of both; and a lead summing network, responsive to said plurality of digital control signals, for adding said selected number of analog input signals and for outputting a set of summed output signals, whereby a set of digital control data bits on said digital control signals selects any combination of analog signals from said analog input signal terminals and analog expansion input signal terminals for processing.

9. The integrated circuit of claim 8 wherein said plurality of analog output signal terminals are coupled to at least some of said plurality of analog input signal terminals through a buffer circuit having a plurality of inputs and outputs, at least some of said plurality of analog input signal terminals coupled to said buffer circuit inputs, and at least some of said plurality of analog output signal terminals being coupled to said buffer circuit outputs.

10. The integrated circuit of claim 8, further comprising a plurality of analog filters for receiving said summed output signals and for filtering said summed output signals to provide a set of filtered signals.

11. The integrated circuit of claim 10 wherein said plurality of analog filters have a plurality of cutoff frequency settings that are individually programmable for each of said plurality of analog filters.

12. The integrated circuit of claim 10, further comprising a plurality of analog amplifiers for receiving and amplifying said set of filtered signals and for outputting a set of amplified signals.

13. The integrated circuit of claim 12 wherein said plurality of analog amplifiers have a plurality of gain settings that are individually programmable for each of said plurality of amplifiers.

14. The integrated circuit of claim 13, further comprising an analog multiplexor with a plurality of analog inputs receiving said set of amplified signals and for selecting and coupling one of said amplified signals as a multiplexor output; and a sample and hold circuit coupled to said multiplexor output to receive said selected one of said amplified signals and, under control of a hold control input, holding the signal level of said selected one of said amplified signals at a substantially constant level.

15. An ECG application specific integrated circuit for monitoring multi-lead ECG signals from a patient, the integrated circuit comprising:

a plurality of analog input signal terminals, at least some of said plurality of input signal terminals being adapted for coupling to a plurality of patient electrodes for receiving ECG input signals from said patient electrodes;

a buffer circuit having a plurality of buffer inputs and buffer outputs, said plurality of buffer inputs coupled to at least some of said plurality of analog input signal terminals, said plurality of buffer outputs providing buffered versions of said ECG input signals;

a plurality of analog output signal terminals coupled to at least some of said plurality of buffer outputs and allowing said ECG input signals to be coupled to an external circuit;

a plurality of analog expansion input signal terminals for inputting analog signals from external analog sources;

a plurality of digital control input signal terminals responsive to a plurality of digital control signals for selecting a number of said plurality of analog signals from either said analog input signal terminals, said analog expansion input signal terminals, or a combination of both, for amplification and processing;

a lead summing network, responsive to said plurality of digital control signals, for adding said selected number of analog input singals and for outputting a set of summed output signals;

a pacer detection circuit responsive to said summed output signals for detecting heart pacemaker pulses and for generating a pacer signal indicating the presence of said pacemaker pulses;

a blanking circuit, responsive to said pacer signal, for blanking said set of summed output signals;

a plurality of analog filters for receiving said summed output signals and for filtering said summed output signals to provide a set of filtered signals;

a plurality of analog amplifiers for receiving and amplifying said set of filtered signals and for outputting a set of amplified signals;

an analog multiplexor with a plurality of analog inputs receiving said set of amplified signals and selecting and coupling one of said amplified signals as a multiplexor output; and a sample and hold circuit coupled to said multiplexor output to receive said selected one of said amplified signals and, under control of a hold control input, holding the signal level of said selected one of said amplified signals at a substantially constant level, whereby a set of digital control data bits on said digital control signals select any combination of analog signals from said analog input signal terminals and analog expansion input signal terminals for amplification and processing.

16. An ECG application specific integrated circuit for monitoring multi-lead ECG signals from a patient, the integrated circuit comprising:

seven analog input signal terminals, at least some of said input signal terminals being adapted for coupling to patient electrodes for receiving ECG input signals from said patient electrodes;

a buffer circuit having a seven buffer inputs and seven buffer outputs, said buffer inputs coupled to said analog input signal terminals, said buffer outputs providing buffered versions of said ECG input signals;

seven analog output signal terminals coupled to said buffer outputs and allowing said ECG input signals to be coupled to an external circuit;

seven analog expansion input signal terminals for inputting analog expansion signals from external analog sources;

a plurality of digital control input signal terminals responsive to a plurality of digital control signals for selecting a number of said analog signals from either said analog input signal terminals, said analog expansion input signal terminals, or a combination of both, for amplification and processing;

a lead summing network, responsive to said plurality of digital control signals, for adding said selected number of analog input signals and for outputting a set of summed output signals;

a plurality of analog filters for receiving said summed output signals and for filtering said summed output signals to provide a set of filtered signals;

a plurality of analog amplifiers for receiving and amplifying said set of filtered signals and for outputting a set of amplified signals;

an analog multiplexor with a plurality of analog inputs receiving said set of amplified signals and selecting and coupling one of said amplified signals as a multiplexor output; and a sample and hold circuit coupled to said multiplexor output to receive said selected one of said amplified signals and, under control of a hold control input, holding the signal level of said selected one of said amplified signals at a substantially constant level, whereby a set of digital control data bits on said digital control signals select any combination of analog signals from said analog input signal terminals and analog expansion input signal terminals for amplification and processing.

17. A first and second application specific integrated circuits comprising:

a first set of analog input signal terminals within the first integrated circuit, at least some of said first set of input signal terminals receiving a first set of input signals from external analog sources;

a buffer circuit within the first integrated circuit receiving said first set of input signal terminals and providing a first set of buffered outputs for each of said first set of input signals;

a first set of analog output signal terminals within the first integrated circuit coupled to said buffered outputs allowing said first set of input signals to be coupled to an external circuit;

a first set of analog expansion input signal terminals within the first integrated circuit for inputting a first set of analog expansion signals from external analog sources;

a first set of digital control input signal terminals responsive to a first set of digital control signals within the first integrated circuit for selecting a number of analog signals from either said first set of analog input signal terminals, said first set of analog expansion input signal terminals, or a combination of both;

a first lead summing network within the first integrated circuit, responsive to said first set of digital control signals, for adding said selected number of analog input signals and for outputting a first set of summed output signals;

a second set of analog input signal terminals within the second integrated circuit, which may or may not be receiving a second set of input signals from external analog sources;

a buffer circuit within the second integrated circuit receiving said second set of input signal terminals and providing buffered outputs for each of said second set of input signals;

a second set of analog output signal terminals within the second integrated circuit coupled to said set of buffered output allowing said second set of input signals to be coupled to an external circuit;

a second set of analog expansion input signal terminals within the second integrated circuit for inputting a second set of analog expansion signals from external analog sources, including said first set of analog output signal terminals;

a second set of digital control input signal terminals responsive to a second set of digital control signals within the second integrated circuit for selecting a number of analog signals from either said second set of analog input signal terminals, said second set of analog expansion input signal terminals, or a combination of both; and a second lead summing network within the second integrated circuit, responsive to said second set of digital control signals, for adding said selected number of analog input signals and for outputting a second set of summed output signals, whereby the first and second integrated circuits produce a combination of analog signals from said first and second sets of analog input signal terminals and said first and second sets of analog expansion input signal terminals in response to a first and second set of digital control data bits on said first and second sets of digital control signals.

18. A first and second application specific integrated circuits for monitoring multi-lead physiological signals from a patient, comprising:

a first set of analog input signal terminals within the first integrated circuit, at least some of said first set of input signal terminals being coupled to the patient and receiving a first set of input signals from the patient;

a first set of analog output signal terminals within the first integrated circuit coupled to at least some of said first set of analog input signal terminals and allowing said first set of input signals to be coupled to an external circuit;

a first set of analog expansion input signal terminals within the first integrated circuit for inputting a first set of analog expansion signals from external analog sources;

a first set of digital control input signal terminals responsive to a first set of digital control signals within the first integrated circuit for selecting a number of analog signals from either said first set of analog input signal terminals, said first set of analog expansion input signal terminals, or a combination of both;

a first lead summing network within the first integrated circuit, responsive to said first set of digital control signals, for adding said selected number of analog input signals and for outputting a first set of summed output signals;

a second set of analog input signal terminals within the second integrated circuit, some of which may or may not be coupled to the patient and receiving a second set of input signals from the patient a second set of analog output signal terminals within the second integrated circuit coupled to at least some of said second set of analog input signal terminals and allowing said second set of input signals to be coupled to an external circuit;

a second set of analog expansion input signal terminal within the second integrated circuit for inputting a second set of analog expansion signals from external analog sources, including said first set of analog output signal terminals;

a second set of digital control input signal terminals responsive to a second set of digital controls signals within the second integrated circuit for selecting a number of analog signals from either said second set of analog input signal terminals, said second set of analog expansion input signal terminals, or a combination of both; and a second lead summing network within the second integrated circuit, responsive to said second set of digital control signals, for adding said selected number of analog input signals and for outputting a second set of summed output signals, whereby the first and second integrated circuits produce a combination of analog signals from said first and second sets of analog input signal terminals and said first and second sets of analog expansion input signal terminals in response to a first and second set of digital control data bits on said first and second sets of digital control signals.

19. The integrated circuit of claim 18 wherein said first set of analog output signal terminals are coupled to at least some of said first set of analog input signal terminals through a first buffer circuit having a plurality of inputs and outputs, at least some of said first set of analog input signal terminals coupled to said first buffer circuit inputs, and at least some of said first set of analog output signal terminals being coupled to said first buffer circuit outputs.

20. The integrated circuit of claim 18 wherein said second set of analog output signal terminals are coupled to at least some of said second set of analog input signal terminals through a second buffer circuit having a plurality of inputs and outputs, at least some of said second set of analog input signal terminals coupled to said second buffer circuit inputs, and at least some of said second set of analog output signal terminals being coupled to said second buffer circuit outputs.

21. The integrated circuit of claim 18, further including a plurality of analog filters within the first integrated circuit for receiving said first set of summed output signals and for filtering said first set of summed output signals and outputting a first set of filtered signals.

22. The integrated circuit of claim 21 wherein said plurality of analog filters have a plurality of cutoff frequency settings that are individually programmable for each of said plurality of analog filters.

23. The integrated circuit of claim 21, further including a plurality of analog amplifiers for receiving and amplifying said set of filtered signals and for outputting a set of amplified signals.

24. The integrated circuit of claim 23 wherein said plurality of analog amplifiers have a plurality of gain settings that are individually programmable for each of said plurality of amplifiers.

25. The integrated circuit of claim 23, further comprising an analog multiplexor with a plurality of analog inputs for receiving said set of amplified signals and selecting and coupling one of said amplified signals as a multiplexor output; and a sample and hold circuit coupled to said multiplexor output to receive said selected one of said amplified signals and, under control of a hold control input, holding the signal level of said selected one of said amplified signals at a substantially constant level.

26. The integrated circuit of claim 18, further including a plurality of analog filters within the second integrated circuit receiving said second set of summed output signals and for filtering said second set of summed output signals and outputting a second set of filtered signals.

27. The integrated circuit of claim 26 wherein said plurality of analog filters have a plurality of cutoff frequency settings that are individually programmable for each of said plurality of analog filters.

28. The integrated circuit of claim 26, further compromising a plurality of analog amplifiers for receiving and amplifying said set of filtered signals and for outputting a set of amplified signals.

29. The integrated circuit of claim 28 wherein said plurality of analog amplifiers have a plurality of gain settings that are individually programmable for each of said plurality of amplifiers.

30. The integrated circuit of claim 28, further including an analog multiplexor with a plurality of analog inputs for receiving said set of amplified signals and selecting and coupling one of said amplified signals as a multiplexor output; and
  a sample and hold circuit coupled to said multiplexor output to receive said selected one of said amplified signals and, under control of a hold control input, holding the signal level of said selected one of said amplified signals at a substantially constant level.

31. A first and second ECG application specific integrated circuit for monitoring multi-lead ECG signals from a patient, comprising:
  a first set of analog input signal terminals within the first integrated circuit, at least some of said first set of input signal terminals being adapted for coupling to a plurality of patient electrodes for receiving a first set of ECG input signals from said plurality of patient electrodes;
  a first set of analog output signal terminals within the first integrated circuit coupled to at least some of said first set of analog input signal terminals and allowing said first set of input signals to be coupled to an external circuit;
  a first set of analog expansion input signal terminals within the first integrated circuit for inputting a first set of analog expansion signals from external analog sources;
  a first set of digital control input signal terminals responsive to a first set of digital control signals within the first integrated circuit for selecting a number of analog signals from either said first set of analog input signal terminals, said first set of analog expansion input signal terminals, or a combination of both;
  a first lead summing network within the first integrated circuit, responsive to said first set of digital control signals, for adding said selected number of analog input signals and for outputting a first set of summed output signals;
  a second set of analog input signal terminals within the second integrated circuit, which may or may not be coupled to said plurality of patient electrodes and receiving a second set of ECG input signals from said plurality of patient electrodes;
  a second set of analog output signal terminals within the second integrated circuit coupled to at least some of said second set of analog input signal terminals and allowing said second set of input signals to be coupled to an external circuit;
  a plurality of analog expansion input signal terminals within the second integrated circuit for inputting analog expansion signals from external analog sources, including said first set of analog output signal terminals;
  a second set of digital control input signal terminals responsive to a second set of digital control signals within the second integrated circuit for selecting a number of analog signals from either said second set of analog input signal terminals, said second set of analog expansion input signal terminals, or a combination of both; and
  a second lead summing network within the second integrated circuit, responsive to said second set of digital control signals, for adding said selected number of analog input signals and for outputting a second set of summed output signals, whereby the first and second integrated circuits produce a combination of analog signals from said first and second sets of analog input signal terminals and said first and second sets of analog expansion input signal terminals in response to a first and second set of digital control data bits on said first and second sets of digital control signals.

32. The integrated circuit of claim 31 wherein said first set of analog output signal terminals are coupled to at least some of said first set of analog input signal terminals through a first buffer circuit having a plurality of inputs and outputs, at least some of said first set of analog input signal terminals coupled to said first buffer circuit inputs, and at least some of said first set of analog output signal terminals being coupled to said first buffer circuit outputs.

33. The integrated circuit of claim 31 wherein said second set of analog output signal terminals are coupled to at least some of said second set of analog input signal terminals through a second buffer circuit having a plurality of inputs and outputs, at least some of said second set of analog input signal terminals coupled to said second buffer circuit inputs, and at least some of said second set of analog output signal terminals being coupled to said second buffer circuit outputs.

34. The integrated circuit of claim 31, further including a plurality of analog filters within the first integrated circuit for receiving said first set of summed output signals and for filtering said first set of summed output signals and outputting a first set of filtered signals.

35. The integrated circuit of claim 34 wherein said plurality of analog filters have a plurality of cutoff frequency settings that are individually programmable for each of said plurality of analog filters.

36. The integrated circuit of claim 34, further including a plurality of analog amplifiers for receiving and amplifying said set of filtered signals and for outputting a set of amplified signals.

37. The integrated circuit of claim 36 wherein said plurality of analog amplifiers have a plurality of gain settings that are individually programmable for each of said plurality of amplifiers.

38. The integrated circuit of claim 36, further comprising an analog multiplexor with a plurality of analog inputs for receiving said set of amplified signals and selecting and coupling one of said amplified signals as a multiplexor output; and
  a sample and hold circuit coupled to said multiplexor output to receive said selected one of said amplified signals and, under control of a hold control input, holding the signal level of said selected one of said amplified signals at a substantially constant level.

39. The integrated circuit of claim 31, further including a plurality of analog filters within the second integrated circuit for receiving said second set of summed output signals and for filtering said second set of summed output signals and outputting a second set of filtered signals.

40. The integrated circuit of claim 39 wherein said plurality of analog filters have a plurality of cutoff frequency settings that are individually programmable for each of said plurality of analog filters.

41. The integrated circuit of claim 39, further comprising a plurality of analog amplifiers for receiving and amplifying said set of filtered signals and for outputting a set of amplified signals.

42. The integrated circuit of claim 41 wherein said plurality of analog amplifiers have a plurality of gain settings that are individually programmable for each of said plurality of amplifiers.

43. The integrated circuit of claim 41, further including an analog multiplexor with a plurality of analog inputs for receiving said set of amplified signals and selecting and coupling one of said amplified signals as a multiplexor output; and
   a sample and hold circuit coupled to said multiplexor output to receive said selected one of said amplified signals and, under control of a hold control input, holding the signal level of said selected one of said amplified signals at a substantially constant level.

44. A multi-lead ECG amplifier integrated circuit with improved radio frequency interference immunity for monitoring multi-lead ECG signals from a patient, the circuit comprising:
   an integrated circuit substrate with a reduced ground plane area for reducing capacitive coupling to a chassis and AC line neutral;
   a plurality of analog input signal terminals, at least some of said plurality of input signal terminals being adapted for coupling to a plurality of patient electrodes for receiving ECG input signals from said patient electrodes;
   a buffer circuit having a plurality of buffer inputs and buffer outputs, said plurality of buffer inputs coupled to at least some of said plurality of analog input signal terminals, said plurality of buffer outputs providing buffered versions of said ECG input signals;
   a plurality of analog output signal terminals coupled to at least some of said plurality of buffer outputs and allowing said ECG input signals to be coupled to an external circuit;
   a plurality of analog expansion input signal terminals for inputting expansion analog signals from external analog sources;
   a plurality of digital control input signal terminals responsive to a plurality of digital control signals for selecting a number of said plurality of analog signals from either said analog input signal terminals, said analog expansion input signal terminals, or a combination of both, for amplification and processing;
   a lead summing network, responsive to said plurality of digital control signals, for adding said selected number of analog input signals and for outputting a set of summed output signals;
   a plurality of analog filters for receiving said summed output signals and for filtering summed output signals for outputting a set of filtered signals;
   a plurality of analog amplifiers for receiving and amplifying said set of filtered signals and for outputting a set of amplified signals;
   an analog multiplexor with a plurality of analog inputs receiving said set of amplified signals and selecting and coupling one of said amplified signals as a multiplexor output; and
   a sample and hold circuit coupled to said multiplexor output to receive said selected one of said amplified signals and, under control of a hold control input, holding the signal level of said selected one of said amplified signals at a substantially constant level, whereby a set of digital control data bits on said digital control signals selects a combination of analog signals from said analog input signal terminals and analog expansion input signal terminals for processing.

45. An ECG application specific integrated circuit with pacer pulse detection circuitry for monitoring multi-lead ECG signals from a patient, the integrated circuit comprising:
   a plurality of analog input signal terminals, at least some of said plurality of input signal terminals being coupled to a plurality of patient electrodes and receiving ECG input signals from said patient electrodes;
   a lead summing network responsive to a digital control input signal for adding a selected number of said ECG input signals and providing a set of summed output signals; and
   a multiplexor selecting a first one of said set of summed output signals containing a pacemaker signal.

46. The circuit of claim 45, further including a blanking circuit blanking the ECG signals for a first predetermined time or a second predetermined time, said first predetermined time corresponding to said first type of pacer pulse, said second predetermined time corresponding to said second type of pacer pulse.

47. The circuit of claim 45 wherein said filter is a bandpass filter to remove unwanted ECG signals and respiration monitor signals.

48. The circuit of claim 45, further including means for automatically switching said multiplexor to select a second one of said summed output signals if one of said plurality of patient electrodes used by said lead summing network to provide said first one of said set of summed output signals becomes disconnected from the patient.

49. A pacer pulse detection circuit for monitoring ECG signals from a patient and detecting heart pacemaker pulses, the circuit comprising:
   a filter for passing pacemaker signals and for producing filtered pacer signals;
   a differentiator for receiving said filtered pacer signals and for producing a positive spike and a negative spike;
   a plurality of comparators for comparing said positive spike with a predetermined positive threshold and said negative spike with a predetermined negative threshold; and
   a timer for measuring elapsed time between said spikes and for determining whether said pacer signal is a first type of pacer pulse or a second type of pacer pulse, whereby the ECG signal can be blanked for a period of time corresponding to the duration of said first type of pacer pulse or said second type of pacer pulse.

50. The circuit of claim 49, further comprising a blanking circuit for blanking the ECG signals for a first predetermined time or a second predetermined time, said first predetermined time corresponding to said first type of pacer pulse, said second predetermined time corresponding to said second type of pacer pulse.

51. The circuit of claim 49 wherein said filter is a bandpass filter to remove unwanted ECG signals and respiration monitor signals.

52. The circuit of claim 50, further comprising means for selecting a first ECG lead from the ECG signals to monitor for pacer pulses from a plurality of ECG leads provided to the pacer pulse detection circuit.

53. The circuit of claim 51, further comprising means for automatically switching from said first ECG lead to a second of said plurality of ECG leads if said first ECG lead becomes disconnected from the patient.

54. An ECG application specific integrated circuit with pacer pulse detection circuitry for monitoring multi-lead ECG signals from a patient, the integrated circuit comprising:
- a plurality of analog input signal terminals, at least some of said plurality of input signal terminals being coupled to a plurality of patient electrodes and receiving ECG input signals from said patient electrodes;
- a plurality of analog expansion input signal terminals for inputting analog signals from external analog sources;
- a plurality of digital control input signal terminals responsive to a plurality of digital control signals for selecting a number of said plurality of analog signals from either said analog input signal terminals, said analog expansion input signal terminals, or a combination of both, for amplification and processing; and
- a lead summing network, responsive to said plurality of digital control signals, for adding said selected number of analog input signals and for outputting a set of summed output signals;
- a multiplexor for selecting and multiplexing a first one of said set of summed output signals containing a pacemaker signal;
- a filter for passing said pacemaker signal and for producing a filtered pacer signal;
- a differentiator for receiving said filtered pacer signal and for producing a positive spike and a negative spike;
- a plurality of comparators for comparing said positive spike with a predetermined positive threshold and said negative spike with a predetermined negative threshold; and
- a timer for measuring elapsed time between said spikes and for determining whether said pacer signal is a first type of pacer pulse or a second type of pacer pulse; and
- a blanking circuit for blanking said set of summed output signals for a first predetermined time or a second predetermined time, said first predetermined time corresponding to said first type of pacer pulse, said second predetermined time corresponding to said second type of pacer pulse.

55. The circuit of claim 54, further comprising means for automatically switching said multiplexor from first ECG lead to a second of said plurality of ECG leads if said first ECG lead becomes disconnected from the patient.

56. An ECG application specific integrated circuit for monitoring multi-lead ECG signals from a patient, the integrated circuit comprising:
- seven analog input signal terminals, at least some of said input signal terminals being adapted for coupling to patient electrodes for receiving ECG input signals from said patient electrodes;
- a buffer circuit having a seven buffer inputs and seven buffer outputs, said buffer inputs coupled to said analog input signal terminals, said buffer outputs providing buffered versions of said ECG input signals;
- seven analog output signal terminals coupled to said buffer outputs and allowing said ECG input signals to be coupled to an external circuit;
- seven analog expansion input signal terminals for inputting analog expansion signals from external analog sources;
- a plurality of digital control input signal terminals responsive to a plurality of digital control signals for selecting a number of said analog signals from either said analog input signal terminals, said analog expansion input signal terminals, or a combination of both, for amplification and processing;
- a lead summing network, responsive to said plurality of digital control signals, for adding said selected number of analog input signals and for outputting a set of summed output signals;
- a pacer detection multiplexor for selecting and multiplexing a first one of said set of summer output signals containing a pacemaker signal;
- a pacer filter for passing said pacemaker signal and for producing filtered pacer signals;
- a differentiator for receiving said filtered pacer signals and for producing a positive spike and a negative spike;
- a plurality of comparators for comparing said positive spike with a predetermined positive threshold and said negative spike with a predetermined negative threshold;
- a timer for measuring elapsed time between said spikes and for determining whether said pacer signal is a first type of pacer pulse or a second type of pacer pulse;
- a controller for receiving said elapsed time and for generating a pacer blanking signal for a period of time corresponding to the duration of said first type of pacer pulse or said second type of pacer pulse;
- a blanking circuit, responsive to said pacer blanking signal, for blanking said set of summed output signals;
- a plurality of analog filters coupled to said blanking circuit for receiving said summed output signals when said set of summed output signals are not blanked by said blanking circuit and for filtering said summed output signals to provide a set of filtered signals;
- a plurality of analog amplifiers for receiving said set of filtered signals and for providing a set of amplified signals;
- an analog multiplexor with a plurality of analog inputs for receiving said set of amplified signals and for selecting and multiplexing one of said amplified signals to a multiplexor output; and
- a sample and hold circuit coupled to said multiplexor output to receive said selected one of said amplified signals and, under control of a hold control input, holding the signal level of said selected one of said amplified signals at a substantially constant level, whereby a set of digital control data bits on said digital control signals select any combination of analog signals from said analog input signal terminals and analog expansion input signal terminals for amplification and processing.

57. The circuit of claim 56 wherein said pacer filter is a bandpass filter to remove unwanted ECG signals and respiration monitor signals.

58. The circuit of claim 56, further comprising means for automatically switching said pacer detection multiplexor to select a second one of said set of summed output signals if one of said plurality of patient electrodes used by said lead summing network to provide said first one of said set of summed output signals becomes disconnected from the patient.

* * * * *

UNITED STATES PATENT AND TRADEMARK OFFICE
CERTIFICATE OF CORRECTION

PATENT NO. : 5,231,990
DATED : August 3, 1993
INVENTOR(S) : Karl F. Gauglitz

It is certified that error appears in the above-identified patent and that said Letters Patent is hereby corrected as shown below:

On the title page, and in column 1, in the first line of the title, delete "SPECTIFIC" and substitute therefor --SPECIFIC--.

In column 19, claim 15, line 5, please delete "singals" and substitute therefor --signals--.

In column 20, claim 17, line 52, after "to said" and before "set of", please insert --second--.

In column 20, claim 17, line 53, please delete "output" and substitute therefor --outputs--.

In column 21, claim 18, line 49, please delete "terminal" and substitute therefor --terminals--.

In column 21, claim 18, line 55, please delete "controls" and substitute therefor --control--.

In column 26, claim 53, line 65, please delete "51" and substitute therefor --52--.

Signed and Sealed this

Fifteenth Day of March, 1994

BRUCE LEHMAN

Attest:

Attesting Officer

Commissioner of Patents and Trademarks